(12) United States Patent
Hwang et al.

(10) Patent No.: US 7,202,359 B2
(45) Date of Patent: Apr. 10, 2007

(54) AZAOXA HETEROCYCLIC COMPOUND AND METHOD OF PREPARING THE SAME

(75) Inventors: Kuen-Yuan Hwang, Hsinchu (TW); An-Pang Tu, Hsinchu (TW); Shyh Haw Liao, Hsinchu (TW)

(73) Assignee: Chang Chun Plastics Co., Ltd., Taipei (TW)

( * ) Notice: Subject to any disclaimer, the term of this patent is extended or adjusted under 35 U.S.C. 154(b) by 12 days.

(21) Appl. No.: 10/982,589

(22) Filed: Nov. 4, 2004

(65) Prior Publication Data

US 2005/0085634 A1   Apr. 21, 2005

Related U.S. Application Data

(62) Division of application No. 10/630,195, filed on Jul. 29, 2003, now abandoned.

(30) Foreign Application Priority Data

Oct. 3, 2002   (TW) .............................. 91122816 A

(51) Int. Cl.
*C07D 265/02* (2006.01)
(52) U.S. Cl. ...................................................... 544/73
(58) Field of Classification Search .................. 544/73
See application file for complete search history.

(56) References Cited

U.S. PATENT DOCUMENTS

| | | | | |
|---|---|---|---|---|
| 4,278,733 A | * | 7/1981 | Benzinger | 428/413 |
| 5,021,484 A | * | 6/1991 | Schreiber et al. | 524/100 |
| 5,044,074 A | * | 9/1991 | Hadwiger et al. | 29/848 |
| 5,151,939 A | * | 9/1992 | Marrah et al. | 381/15 |
| 5,176,780 A | * | 1/1993 | Schreiber et al. | 156/307.3 |
| 5,443,911 A | * | 8/1995 | Schreiber et al. | 428/413 |
| 5,543,516 A | * | 8/1996 | Ishida | 544/69 |
| 5,566,695 A | * | 10/1996 | Levey et al. | 134/83 |
| 6,005,064 A | | 12/1999 | Hirai et al. | |

\* cited by examiner

*Primary Examiner*—Thurman K. Page
*Assistant Examiner*—Chukwuma Nwaonicha
(74) *Attorney, Agent, or Firm*—Fulbright & Jaworski L.L.P.

(57) ABSTRACT

Disclosed is an azaoxa heterocyclic compound represented by the following formula (I):

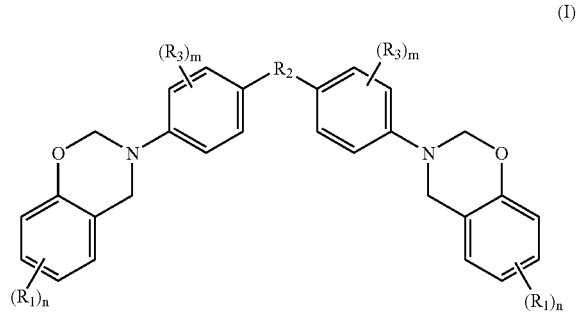

(wherein, each symbol is defined the same as in the specification) and a method for preparing the same. This compound of the present invention is prepared by the reaction of a phenolic compound, an aromatic diamine compound and an aldehyde compound. The azaoxa heterocyclic compound of the present invention can be used as a hardening resin or a hardener for an epoxy resin, polyether and a resin containing active hydrogen atoms, wherein the composition formed by the azaoxa heterocyclic compound and the epoxy resin is useful in the application of laminates, adhesive, semiconductor packaging materials and phenolic resin forming materials.

11 Claims, 6 Drawing Sheets

AZAOXA HETEROCYCLIC COMPOUND AND METHOD OF PREPARING THE SAME

U.S. application Ser. No. 10/982,589 is a Div. 10/630,195 filed Jul. 29, 2003 now abandoned.

FIELD OF THE INVENTION

The present invention relates to an azaoxa heterocyclic compound used as a hardening resin or a hardener for an epoxy resin, polyether and a resin containing active hydrogen atoms and a method for preparing the azaoxa heterocyclic compound.

BACKGROUND OF THE INVENTION

Thermosetting resins, such as phenolic resins, melainine resins, epoxy resins, unsaturated polyester resins, bismaleimide resins and the like, are widely applied in a variety of industry fields. However, these resins still suffer from many disadvantages, for example, the generation of volatile byproducts on curing of phenolic resins or melamine resins, the poor inflammability of epoxy resins and unsaturated polyester resins and the extremely high price of bismaleimide resins. To solve the above problems, there have been made attempts to develop the thermosetting resins having the benzoxazine cyclic structure.

The resin having the benzoxazine cyclic structure has become another choice of the thermosetting resins since the thermal stability of such a resin is similar to that of phenolic resins, epoxy resins and other thermosetting resins. The thermosetting resins having the benzoxazine cyclic structure are cured by the ring-opening polymerization of the benzoxazine rings. Generally, the compounds having the benzoxazine cyclic structure is prepared by the reaction of a phenolic compound, an amine compound and an aldehyde compound. But many patents disclose the method for preparing the compounds having the benzoxazine cyclic structure, which are prepared by the reaction of aniline and phenolic compound. U.S. Pat. No. 6,005064 disclosed the thermosetting resin having the benzoxazine cyclic structure prepared by the reaction of a phenolic resin, formaldehyde and aniline; and JP-A-Hei-11-50123 also disclosed the method for preparing dihydrobenzoxazine thermosetting resin from bisphenol, aniline and formalin and using methyl ethyl acetone as a solvent. However, aniline used in these preparing method is toxic, and is a forbidden chemical material by the law. The preparation method cannot meet the requirements with the mass production in industry.

JP-A-Hei-11-50123 discloses a method for preparing dihydrobenzoxazine thermosetting resin by using methanol as a solvent and undergoing the reaction of phenol, 4,4'-diaminodiphenylmethane and paraformaldehyde. This patent only mentioned that phenol is used as a reactant, but not mentioned that a relatively pure azaoxa heterocyclic compound can be prepared by reacting phenolic compound having substituent such as alkyl, alkoxy, alkenyl groups and the like with aromatic diamine. Furthermore, methanol used in the preparing method has high polarity and has relatively large dielectric constant. When methanol is miscible with reactants in an autoclave, the gelation easily occurs and an agglomeration is formed, which results in the instability of the reaction system. On the other hand, if the temperature-control is improper in the reaction system, the compound having the benzoxazine cyclic structure formed by the condensation will further undergo polymerization due to the ring opening at the high temperature., thus resulting in low productivity and a failed reaction.

As described above, many published references disclosed the method for preparing the compound having the benzoxazine cyclic structure. However, these references all did not mention that a particular solvent is used to improve the stability of the reaction system. Therefore, the present inventors have conducted extensive studies in order to overcome the above mentioned problems. As a result, they have found that the system was endowed with relatively high stability as using the hydrocarbon solvent to conduct the reaction of phenolic compounds, aromatic diamines and aldehyde compounds. In addition to preventing the ring-reopening polymerization at high temperature due to improper temperature control, the present invention prevents the gelation or agglomeration caused by using high polar solvent or protic solvent to undergo the reaction. The azaoxa heterocyclic compound having the benzoxazine cyclic structure obtained is pure and has low water absorbency if the reaction is conducted by using a substituted phenolic compound (particularly alkyl phenolic compound) and an aromatic diamine compound as reactants instead of using high toxic aniline. The azaoxa heterocyclic compound is particularly useful in preparing laminates (CCL), copper foil adhesives, semiconductor packaging materials and phenolic resin forming materials.

SUMMARY OF THE INVENTION

The present invention provides an azaoxa heterocyclic compound represented by the following formula (I):

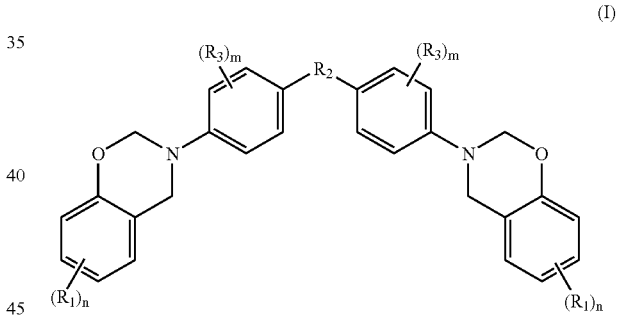

wherein, $R_1$, $R_2$, $R_3$, m and n is defined as the following detailed description section.

It is another object of the present invention to provide a method for preparing azaoxa heterocyclic compounds having the benzoxazine cyclic structure. The method is characterized by using a phenolic compound, an amine compound and an aldehyde compound as reactants in a hydrocarbon solvent to coundergo the reaction.

DETAILED DESCRIPTION OF THE INVENTION

Figure 1:
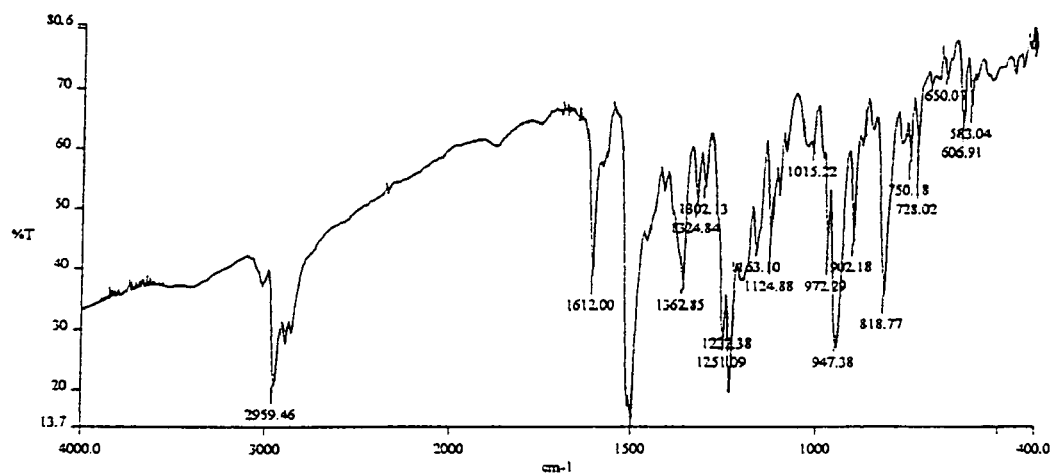
FIG. 1 is an IR spectrum of the azaoxa heterocyclic compound obtained in Example 1 according to the present invention.

The present invention provides an azaoxa heterocyclic compound represented by the following formula (I):

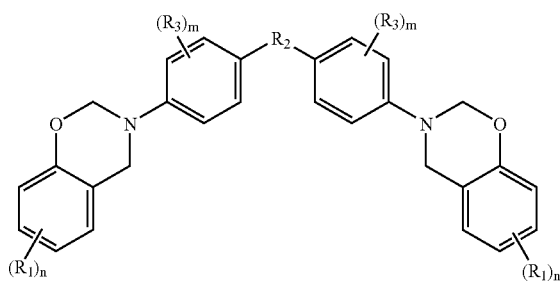

(I)

wherein, $R_1$ represents one selected from the group consisting of an alkyl group, an alkenyl group, an alkoxyl group, a hydroxy group, halogen and an amino group, $R_2$ represents one selected from the group consisting of a bond, an alkylene group, O, S and $SO_2$, and $R_3$ represents H or $C_{1-6}$ alkyl group; m is an integer of 0 to 4; and n is an integer of 1 to 4.

In the azaoxa heterocyclic compounds represented by the above formula (I), the alkyl group represented by $R_1$ and $R_2$ means linear, branched or cyclic alkyl of 1 to 6 carbon atoms, examples thereof include methyl, ethyl, n-propyl, isopropyl, n-butyl, s-butyl, t-butyl, amyl, hexyl, 2-ethylhexyl, cyclohexyl and the like. Alkoxy group means linear, branched or cyclic alkoxyl of 1 to 6 carbon atoms, examples thereof include methoxy, ethoxy, propoxy, isopropoxy, butoxy, s-butoxy, t-butoxy, amoxy, hexoxy, cyclohexoxy and the like. Alkylene group means linear, branched or cyclic alkylene group of 1 to 6 carbon atoms, examples thereof include methylene, ethylene, propylene, butylene, 2-methylpropylene, amylene, 2,2'-dimethyl propylene, hexylene, 2,3-dimethylbutylene and the like.

The azaoxa heterocyclic compounds of the present invention are prepared by the reaction of a phenolic compound, an amine compound and an aldehyde compound in a hydrocarbon solvent.

The phenolic compounds used for preparing the azaoxa heterocyclic compound of the present invention is represented by the following formula (II):

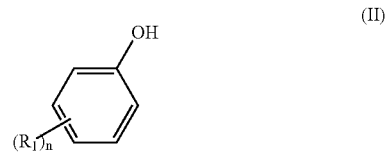

(II)

wherein $R_1$ and n are as defined above.

The preferred phenolic compounds used for preparing the azaoxa heterocyclic compound of the present invention are alkylphenolic compounds. The azaoxa heterocyclic compound having the benzoxazine cyclic structure obtained by using an alkylphenolic compound as a reactant is purer and has low water absorbency, which is particularly useful in preparing a variety of materials used in electronic application.

Examples of the above-mentioned alkylphenol include, but are not limited to, cresol, ethylphenol, propylphenol, butylphenol, s-butylphenol, t-butylphenol, amylphenol, isoamylphenol, hexylphenol, cyclohexylphenol, allylphenol, 2-hydroxy-4-cresol, 3-hydroxy-4-cresol, 2-hydroxy-4-ethylphenol, 3-hydroxy-4-ethylphenol, 2-hydroxy-4-propylphenol, 3-hydroxy-4-propylphenol, 3-hydroxy-4-propylphenol, 3-fluoro-4-cresol, 2-bromo-4-cresol, 3-bromo-4-cresol, 2-fluoro-4-ethylphenol, 3-fluoro-4-ethylpheno, 2-chloro-4-ethylphenol, 3-chloro-4-ethylphenol, 2-bromo-4-ethylphenol, 3-bromo-4-ethylphenol, 2-amino-4-cresol, 3-amino-4-cresol, 2-amino-4-ethlphenol, 2-amino-4-cresol, 3-amino-4-cresol, 2-amino-4-ethylphenol, 3-amino-4-ethylphenol, 2-amino-4-propylphenol, 3-amino-4-propylphenol and the like.

Examples of the alkylphenolic compounds which may be substituted with a hydroxymethyl group include 4-hydroxymethyl-2-cresol, 4-hydroxymethyl-3-cresol, 4-hydroxymethyl-2-ethylphenol, 4-hydroxymethyl-3-ethylphenol, 4-hydroxymethyl-2-n-propylphenol, 4-hydroxymethyl-3-n-propylphenol, 4-hydroxymethyl-2-isopropylphenol,4-4-hydroxymethyl-3-isopropylphenol, 4-hydroxymethyl-2-n-butylphenol, 4-hydroxymethyl-3-n-butylphenol, 4-hydroxymethyl-2-s-butylphenol, 4-hydroxymethyl-3-s-butylphenol, 4-hydroxymethyl-2-t-butylphenol, 4-hydroxymethyl-3-t-butylphenol, 4-hydroxymethyl-2,3-dimethylphenol, 4-hydroxymethyl-2,5-dimethylphenol, 4-hydroxymethyl-3,5-dimethylphenol, 4-hydroxymethyl-2,3,5-trimethylphenol and the like.

Examples of the alkylphenolic compounds which may be substituted with an isopropyl group include 4-isopropyl-2-cresol, 4-isopropyl-3-cresol, 4-isopropyl-2-ethylphenol, 4-isopropyl-3-ethylphenol, 4-isopropyl-2-n-propylphenol, 4-isopropyl-3-n-propylphenol, 2,4-diisopropylphenol, 3,4-diisopropylphenol, 4-isopropyl-2-n-butylphenol, 4-isopropyl-3-n-butylphenol, 4-isopropyl-2-s-butylphenol, 4-isopropyl-3-s-butylphenol, 4-isopropyl-2-t-butylphenol, 4-isopropyl-3-t-butylphenol, 4-isopropyl-2,3-dimethylphenol, 4-isopropyl-2,5-dimethylphenol, 4-isopropyl-3,5-dimethylphenol, 4-isopropyl-2,3,5-trimethylphenol and the like.

Examples of the alkylphenolic compounds which may be substituted with a vinyl group include 4-vinyl-2-cresol, 4-vinyl-3-cresol, 4-vinyl-2-ethylphenol, 4-vinyl-3-ethylphenol, 4-vinyl-2-n-propylphenol, 4-vinyl-3-n-propylphenol, 4-hydroxymethyl-2-isopropylphenol, 4-vinyl-3-isopropylphenol, 4-vinyl-2-n-butylphenol, 4-vinyl-3-n-butylphenol, 4-vinyl-2-s-butylphenol, 4-vinyl-3-s-butylphenol, 4-vinyl-2-t-butylphenol, 4-vinyl-3-t-butylphenol, 4-vinyl-2,3-dimethylphenol, 4-vinyl-2,5-dimethylphenol, 4-vinyl-3,5-dimethylphenol, 4-vinyl-2,3,5-trimethylphenol and the like.

Examples of the alkylphenolic compounds which may be substituted with an amino group include 4-amino-2-cresol, 4-amino-3-cresol, 4-amino-2-ethylphenol, 4-amino-3-ethylphenol, 4-amino-2-n-propylphenol, 4-amino-3-n-propylphenol, 4-amino-2-isopropylphenol, 4-amino-3-isopropylphenol, 4-amino-2-n-butylphenol, 4-amino-3-n-butylphenol, 4-amino-2-s-butylphenol, 4-amino-3-s-butylphenol, 4-amino-2-t-butylphenol, 4-amino-3-t-butylphenol, 4-amino-2,3-dimethylphenol, 4-amino-2,5-dimethylphenol, 4-amino-3,5-dimethylphenol, 4-amino-2,3,5-trimethylphenol and the like.

Examples of other phenolic compounds used for preparing the azaoxa heterocyclic compound of the present invention include, but are not limited to, 4-methoxyphenol, 3-methoxyphenol, 2-methoxyphenol, 4-vinylphenol, 3-vinylphenol, 2-vinylphenol, 4-hydroxyphenol, 3-hydroxyphenol, 2-hydroxyphenol, 4-aminophenol, 3-aminophenol, 2-aminophenol, 4-hydroxymethylphenol, 3-hydroxymethylphenol, 2-hydroxymethylphenol, 4-hydroxymethyl-2-hydroxyphenol, 4-hydroxymethyl-3-hydroxyphenol, 4-hydroxymethyl-2,5-difluorophenol, 4-hydroxymethyl-2,5-dichlorophenol, 4-hydroxymethyl-2,5-dibromophenol, 4-isopropyl-2-methoxyphenol, 4-isopropyl-m3-methoxyphenol, 4-isopropyl-2-hydroxyphenol, 4-isopropyl-3-hydroxyphenol, 4-isopropyl-2,5-difluorophenol, 4-isopropyl-2,5-dichlorophenol, 4-isopropyl-2,5-dibromophenol, 4-vinyl-2-methoxyphenol, 4-vinyl-3-methoxyphenol, 4-vinyl-2-hydroxyphenol, 4-vinyl-3-hydroxyphenol, 4-vinyl-2,5-difluorophenol, 4-vinyl-2,5-dichlorophenol, 4-vinyl-2,5-dibromophenol and the like.

The phenolic compounds used for preparing the azaoxa heterocyclic compound of the present invention are not particularly limited. The phenolic compounds can be mono-functional phenolic compounds, bi-functional phenolic compounds and multi-functional phenolic compounds, provided that at least one of hydrogen atoms on ortho-positions to the hydroxy group in the aromatic ring is unsubstituted.

The aromatic diamine compounds used for preparing the azaoxa heterocyclic compound of the present invention is represented by the following formula (III):

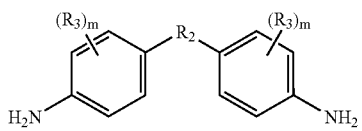

(III)

wherein $R_3$ and m are as defined above.

The aromatic diamine compounds represented by the formula (III) include, but are not limited to, diaminobiphenyl compound, diaminodiphenylalkane compound, diaminodiphenyl ether compound, diaminodiphenyl thioether compound and diaminodiphenyl sulfone compound.

Examples of the diaminobiphenyl compound include, for example, 4,4'-diaminobiphenyl, 4,4'-diamino-2,2'-dimethylbiphenyl, 4,4'-diamino-2,2'-diethylbiphenyl, 4,4'-diamino-2,2'-isopropylbiphenyl, 4,4'-diamino-2,2'-dibutylbiphenyl, 4,4'-diamino-2,2'-di-s-butylbiphenyl, 4,4'-diamino-3,3'-dimethylbiphenyl, 4,4'-diamino-3,3'-diethylbiphenyl, 4,4'-diamino-3,3'-dipropylbiphenyl, 4,4'-diamino-3,3'-diisopropylbiphenyl, 4,4'-diamino-3,3'-dibutylbiphenyl, 4,4'-diamino-3,3'-di-s-butylbiphenyl, 4,4'-diamino-2-butyl-3-methylbiphenyl, 4,4'-diamino-2-butyl-3-ethylbiphenyl, 4,4'-diamino-2-butyl-3-propylbiphenyl, 4,4'-diamino-2'-butyl-3-isopropylbiphenyl, 4,4'-diamino-2-ethyl-3-methylbiphenyl, 4,4'-diamino-2-ethyl-3-propylbiphenyl, 4,4'-diamino-2-ethyl-3-isopropylbiphenyl, 4,4'-diamino-2-methyl-3-propylbiphenyl, 4,4'-diamino-2-methylbiphenyl, 4,4'-diamino-3-isopropylbiphenyl.

Examples of the diaminodiphenylalkane compound include, for example, dianilinomethane, dianilinoethane, dianilinoisopropane, dianilinopropane, 4,4'-methylene bis(2-methylaniline), 4,4'-methylene bis(2-ethylaniline), 4,4'-methylene bis(2-propylaniline), 4,4'-methylene bis(2-isopropylaniline), 4,4'-methylene bis(2-butylaniline), 4,4'-methylene bis(2-s-butylaniline), 4,4'-methylene bis(2-t-butylaniline), 4,4'-methylene bis(2-amylaniline), 4,4'-methylene bis(2-isoamylaniline), 4,4'-methylene bis(2-hexylaniline), 4,4'-ethylene bis(3-methylaniline), 4,4'-ethylene bis(3-ethylaniline), 4,4'-ethylene bis(3-propylaniline), 4,4'-ethylene bis(3-butylaniline), 4,4'-ethylene bis(3-s-butylaniline), 4,4'-ethylene bis(3-t-butylaniline), 4,4'-ethylene bis(3-amylaniline), 4,4'-ethylene bis(3-isoamylaniline), 4,4'-ethylene bis(3-hexylaniline), 4,4'-methylene bis(2,6-dimethylaniline), 4,4'-methylene bis(2,6-diethylaniline), 4,4'-methylene bis(2,6-dipropylaniline), 4,4'-methylene bis(2,6-diisopropylaniline), 4,4'-methylene bis(2,6-dibutylaniline 4,4'-methylene bis(2,6-di-s-butylaniline), 4,4'-methylene bis(2,6-di-t-butylaniline), 4,4'-methylene bis(2,6-diamylaniline), 4,4'-methylene bis(2,6-diisoamylaniline), 4,4'-methylene bis(2,6-dihexylaniline), 4,4'-ethylene bis(2,5-dimethylaniline), 4,4'-ethylene bis(2,5-diethylaniline), 4,4'-ethylene bis(2,5-dipropylaniline), 4,4'-ethylene bis(2,5-diisopropylaniline), 4,4'-ethylene bis(2,5-dibutylaniline), 4,4'-ethylene bis(2,5-di-s-butylaniline), 4,4'-ethylene bis(2,5-di-t-butylaniline), 4,4'-ethylene bis(2,5-diamylaniline), 4,4'-ethylene bis(2,5-diisoamylaniline), 4,4'-ethylene bis(2,5-dihexylaniline), 4,4'-methylene bis(2-butyl-6-methylaniline), 4,4'-methylene bis(2-butyl-6-ethylaniline), 4,4'-methylene bis(2-butyl-6-propylaniline), 4,4'-methylene bis(2-butyl-6-isopropylaniline), 4,4'-methylene bis(2-ethyl-6-methylaniline), 4,4'-methylene bis(2-ethyl-6-propylaniline), 4,4'-methylene bis(2-ethyl-6-isopropylaniline), 4,4'-methylene bis(2-isopropyl-6-methylaniline) and the like.

Examples of the diaminodiphenyl ether compound include, for example, 4,4'-diaminodiphenylether, di(4-amino-3-methylphenyl)ether, di(4-amino-3-ethylphenyl)ether, di(4-amino-3-propylphenyl)ether, di(4-amino-3-isopropylphenyl)ether, di(4-amino-3-butylphenyl)ether, di(4-amino-3-s-butylphenyl)ether, di(4-amino-3-t-butylphenyl)ether, di(4-amino-3-amylphenyl)ether, di(4-amino-3-hexylphenyl)ether, di(4-amino-3,5-dimethylphenyl)ether, di(4-amino-3,5-diethylphenyl)ether, di(4-amino-3,5-dipropylphenyl)ether, di(4-amino-3,5-diisopropylphenyl)ether, di(4-amino-3,5-dibutylphenyl)ether, di(4-amino-3,5-diamylphenyl)ether, di(4-amino-3,5-dihexylphenyl)ether and the like.

Examples of the diaminodiphenyl thioether compound include, for example, 4,4'-diaminodiphenyl thioether, di(4- amino-3-methylphenyl)thioether, di(4-amino-3-ethylphenyl)thioether, di(4-amino-3-propylphenyl)thioether, di(4-amino-3-isopropylphenyl)thioether, di(4-amino-3-butylphenyl)thioether, di(4-amino-3-s-butylphenyl)thioether, di(4-amino-3-t-butylphenyl)thioether, di(4-amino-3-amylphenyl)thioether, di(4-amino-3-hexylphenyl)thioether, di(4-amino-3,5-dimethylphenyl)thioether, di(4-amino-3,5-diethylphenyl)thioether, di(4-amino-3,5-dipropylphenyl)thioether, di(4-amino-3,5-diisopropylphenyl)thioether, di(4-amino-3,5-dibutylphenyl)thioether, di(4-amino-3,5-diamylphenyl)thioether, di(4-amino-3,5-dihexylphenyl)thioether and the like.

Examples of the diaminodiphenyl sulfone compound include, for example, 4,4'-diaminodiphenyl sulfone, di(4-amino-3-methylphenyl)sulfone, di(4-amino-3-ethylphenyl)sulfone, di(4-amino-3-propylphenyl)sulfone, di(4-amino-3-isopropylphenyl)sulfone, di(4-amino-3-butylphenyl)sulfone, di(4-amino-3-s-butylphenyl)sulfone, di(4-amino-3-t-butylphenyl)sulfone, di(4-amino-3-amylphenyl)sulfone, di(4-amino-3-hexylphenyl)sulfone, di(4-amino-3,5-dimethylphenyl)sulfone, di(4-amino-3,5-diethylphenyl)sulfone, di(4-amino-3,5-dipropylphenyl)sulfone, di(4-amino-3,5-diisopropylphenyl)sulfone, di(4-amino-3,5-dibutylphenyl)sulfone, di(4-amino-3,5-diamylphenyl)sulfone, di(4-amino-3,5-dihexylphenyl)sulfone and the like.

The aldehyde compounds used for preparing the azaoxa heterocyclic compounds of the present invention are not particularly limited, provided that the aldehyde compounds are used for preparing the azaoxa heterocyclic compound having the benzoxazine cyclic structure. Examples of the aldehyde compound include, but are not limited to, aldehyde (or vapor thereof), paraformaldehyde, polyoxymethylene and the like.

The azaoxa heterocyclic compounds of the present invention are prepared by the polymerization of a phenolic compound, an aromatic diamine compound, and a aldehyde compound, wherein the phenolic compound, the aromatic diamine compound and the aldehyde compound used in the polymerization are present in a mole ratio of 2:1:4. In comparison to the conventional azaoxa heterocyclic compound having the benzoxazine cyclic structure obtained by using an unalkylated phenolic compound as a reactant, the azaoxa heterocyclic compound of the present invention obtained by using an alkylated phenolic compound as a reactant in polymerization is relatively pure and has relatively low water absorbency. Meanwhile, in the present invention, the azaoxa heterocyclic compounds having the benzoxazine cyclic structure, which may serve as a hardener, are obtained by using an aromatic diamine instead of high toxic aniline as a reactant, thereby favoring mass production.

The hydrocarbon solvents used for preparing the azaoxa heterocyclic compound of the present invention include aliphatic hydrocarbon solvents, alicyclic hydrocarbon solvents, aromatic hydrocarbon solvents or liquid state olefin compounds. The examples of an aliphatic hydrocarbon solvent include, but are not limited to, butane, isobutane, tetramethylbutane, pentane, ethylpentane, trimethylpentane, hexane, methylhexane, ethylhexane, dimethylhexane, heptane, methylheptane, octane, nonane, decane, hexadecane, octodecane and the like. The examples of an alicyclic hydrocarbon solvent include, but are not limited to, cyclopentane, cyclohexane, cyclooctane, cycloheptane, methylcyclopentane, methylcyclohexane, methylcycloheptane and the like. The examples of an aromatic hydrocarbon solvent include, but are not limited to, benzene, toluene, xylene, ethyl benzene, isopropylbenzene, methylisopropylbenzene, naphthalene and the like. The examples of an alicyclic hydrocarbon solvent include, but are not limited to, ethylene, propene, 1-butene, butadiene, cyclopentene, 3-methyl-1-pentene, 4-methyl-1-pentene, 1-hexene, 1,4-hexadiene, 1-octene, 1-decene and the like. Among them, aromatic hydrocarbon solvents are preferred, and toluene and xylene are particularly preferred.

The polar solvents used by the conventional method are, for example, alcohol solvents such as methanol, ethanol, propanol, isopropanol, ethandiol and the like; ether solvents such as 1,2-dimethoxy-ethane, tetrahydrofuran, dioxane and the like; ketone such as acetone, methyl ethyl ketone, methyl isopropyl ketone and the like; and ester solvent such as methyl acetate, ethyl acetate and the like. In comparison to the above polar solvents, the hydrocarbon solvents used in the present invention have relatively low polarity. When these hydrocarbon solvents are used for preparing the compounds having the benzoxazine cyclic structure, the miscibility between the solvent and the reactants is poor. The hydrocarbon solvent can dissolve the phenolic compound and the aromatic diamine compound, but it only can scatter the aldehyde compound so that the agglomeration does not easily occur. Therefore, the stability of the reaction system is enhanced, and thus the formed compounds having the benzoxazine cyclic structure will not further undergo the ring-opening polymerization at very high temperature caused by the improper temperature-control.

Therefore, the present invention provides a method for preparing azaoxa heterocyclic compounds, comprising undergoing the polymerization of a phenolic compound, an amine compound and an aldehyde compound in the hydrocarbon solvent. The phenolic compounds, the amine compounds and the aldehyde compounds used in the present invention are not particularly limited. In addition to the compounds represented by the above formulae (II) and (III), a variety of phenolic compounds, amine compounds and aldehyde compounds for preparing azaoxa heterocyclic compounds having the benzoxazine cyclic structure can be used.

In addition to the phenolic compounds represented by the above formulae (II), phenolic compounds for preparing azaoxa heterocyclic compounds having the benzoxazine cyclic structure include other bi-functional phenolic compounds such as bisphenol A, bisphenol F, bisphenol AD, bisphenol S, tetramethylbisphenol AD, tetramethylbisphenol S, tetramethylbisphenol A, tetramethylbisphenol F, 4',4-bisphenol, 3',3-dimethyl-4,4'-bisphenol, 3',3,5,5'-tetramethyl-4,4'-bisphenol, 4,4'-dihydroxy benzophenone, 4,4'-dihydroxy anthraquinone, 1,6-dihydroxy naphthalene and 2,2'-dihydroxy azabenzene; and multi-functional compound such as tris(4-hydroxyphenyl)methane, tris(4-hydroxyphenyl)ethane, tris(4-hydroxyphenyl)propane, tris(4-hydroxyphenyl)butane, tris(3-methyl-4-hydroxyphenyl)methane, tris(3,5-dimethyl-4-hydroxyphenyl)methane, tetrakis(4-hydroxyphenyl)ethane and tetrakis(3,5-dimethyl-4-hydroxyphenyl)ethane.

In addition to the aromatic diamine compounds represented by the above formulae (III), amine compounds for preparing azaoxa heterocyclic compounds having the benzoxazine cyclic structure can be the primary amine compounds including an unsubstituted aromatic amine compound or a aromatic amine compound substituted with halogen, alkyl groups or alkoxy groups such as aniline, 4-chloroaniline, 4-methylaniline, 4-isopropylaniline, 4-methoxyaniline, 4-ethoxy-2-methylaniline and the like; and a substituted or an unsubstituted aliphatic and alicyclic compounds such as methylamine, ethylamine, ethylenediamine, diethylenediamine, aminocyclohexane, 4-methylaminocyclohexane, 4-methoxyaminocyclohexane, 4,4'-methylene dicyclohexylamine, 2,2'-dimethyl-4,4'-methylene dicyclohexylamine, 1,2-cyclohexanediamine, 1,3-diaminomethylcyclohexane, 2,5-diaminomethylnorbornane and the like.

The method for preparing azaoxa heterocyclic compounds using the hydrocarbon compounds as a solvent renders the system undergoing the reaction under relatively stable conditions, thus effectively solving the conventional agglomeration associated with the miscibility problems due to using high polar protic solvent to undergo the reaction. Furthermore, among them, the aromatic hydrocarbon solvents are preferred, and toluene and xylene are particularly preferred. Such solvents can be recovered below 130° C. after the completion of the reaction, so that the formed azaoxa heterocyclic compound does not further undergo ring-opening reaction at high temperature as recovering the solvent.

The compounds of the present invention prepared by undergoing the reaction of the substituted phenolic compounds and aromatic diamine compounds are examined by IR spectrum. It found that the absorption of the compounds at 3000 to 3500 cm$^{-1}$ is very low, thus proving no large amount of hydroxy groups existing in the compounds. The absorption at 1480 to 1500 cm$^{-1}$ shows 2-substituted structure of a benzene ring, and the absorption at 940 to 950 cm$^{-1}$ and 1220 to 1230 cm$^{-1}$ shows that the C—O—C cyclic structure of acetal is formed. Therefore, the formed azaoxa heterocyclic compound having the benzoxazine cyclic structure is determined.

The present azaoxa heterocyclic compound having the benzoxazine cyclic structure can be used as hardener for epoxy resins, polyester resins or resins having active hydrogen atoms due to the ring-opening polymerization of the benzoxazine cyclic structure. The characteristics of such an azaoxa heterocyclic compound are low viscosity, high thermal stability and low volatility during curing. Such compound is applied for manufacturing CCL, copper foil adhesives, semiconductor packaging materials, phenolic resin forming materials and the like.

The following examples, while not to be construed as limiting in nature, are illustrative of the invention.

EXAMPLES

Example 1

Figure 2:
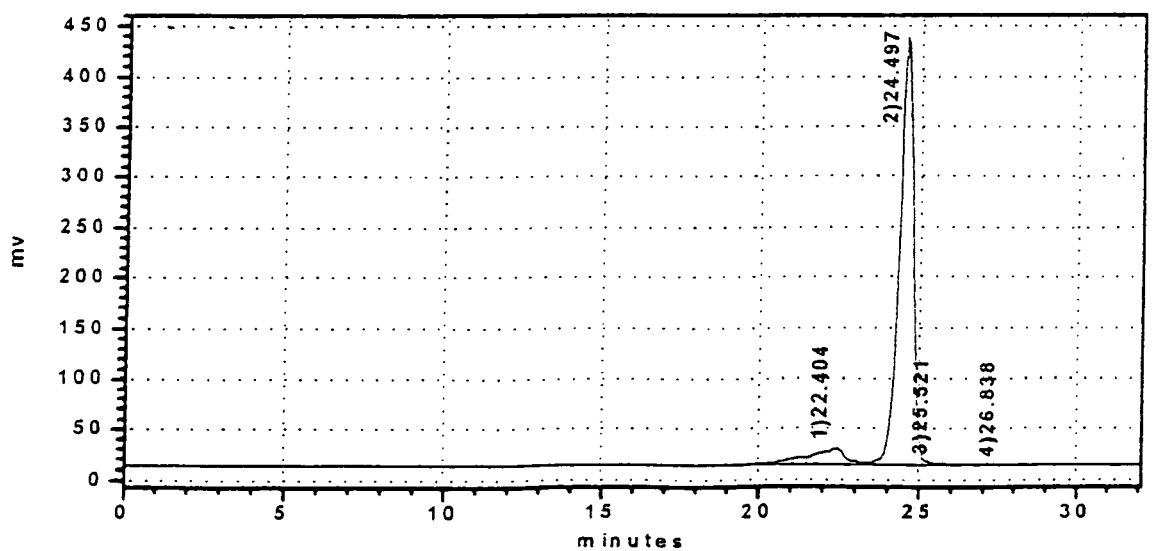
FIG. 2 is a GPC spectrum of the azaoxa heterocyclic compound obtained in Example 1 according to the present invention.

151.4 g of dianilinomethane, 229.5g of p-t-butylphenol, 98.7 g of 92% of paraformaldehyde and 200 g of toluene were successively charged into a 1L of four-neck reaction vessel equipped with a stirrer, thermometer, pressure reducing system, and condensing-heating mantle. After heated up to 80° C., the electric source for heating was shut. The reaction is conducted for 3 hours while maintaining the temperature in the range of 85 and 90° C. Subsequently, in order to recover toluene, the internal pressure was reduced and the temperature was raised. After reaching the temperature of 150° C. and the vacuum pressure of more than 650 mm Hg and after recovering all of toluene, the solid azaoxa heterocyclic compound having the benzoxazine cyclic structure of the present invention was discharged. Alternatively, the solvent can be directly charged into the reaction vessel, and the azaoxa heterocyclic compound was present in a solvent form. The compound was analyzed by Infrared spectroscopy (IR) and gel permeation chromatography (GPC), and the results were shown in FIG. 1 and FIG. 2.

Example 2

Figure 3:
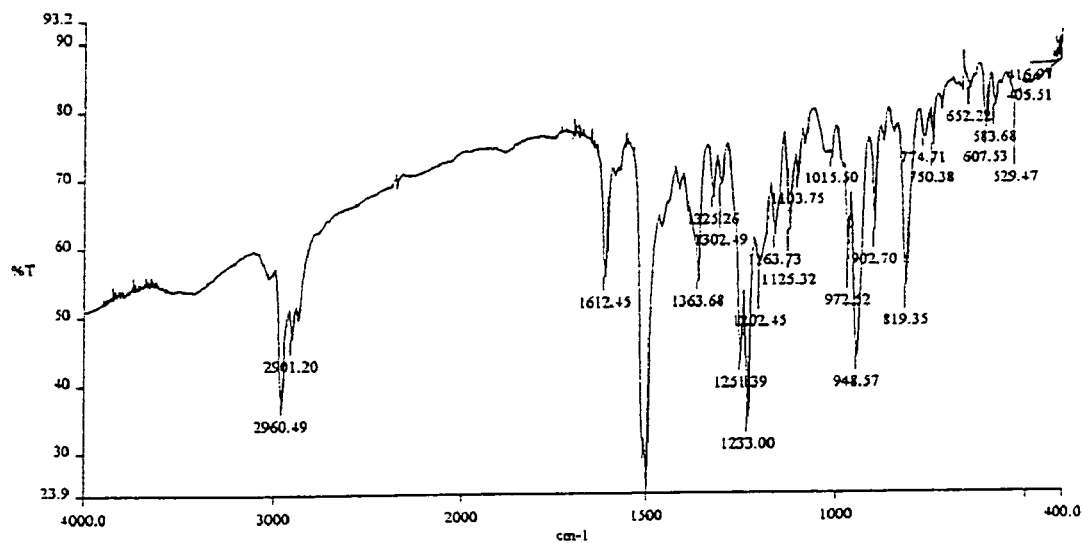
FIG. 3 is an IR spectrum of the azaoxa heterocyclic compound obtained in Example 2 according to the present invention.
Figure 4:
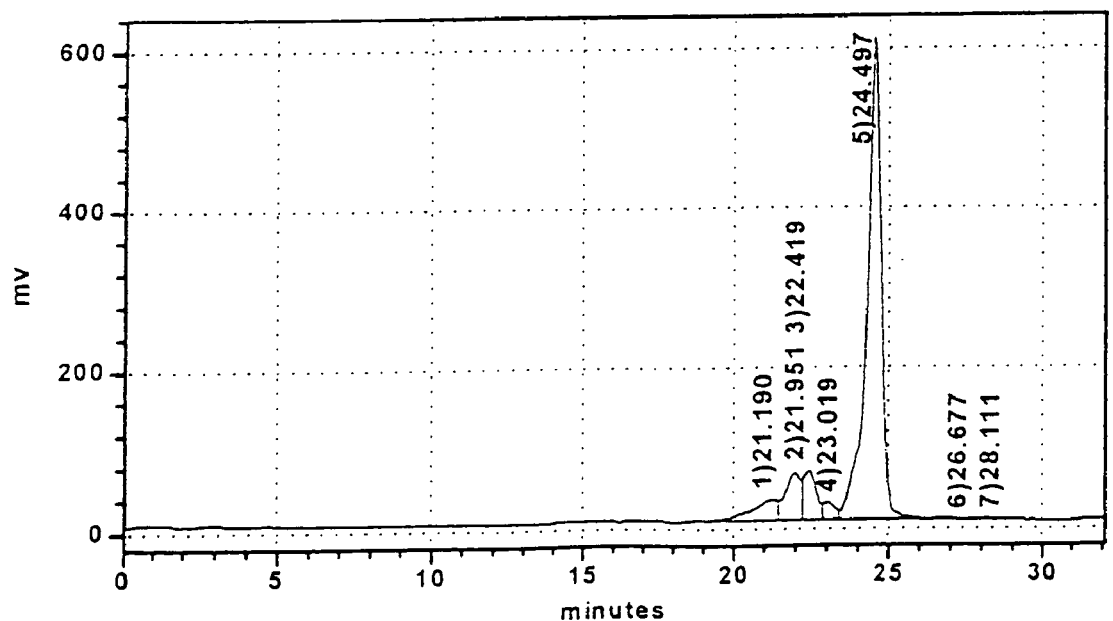
FIG. 4 is a GPC spectrum of the azaoxa heterocyclic compound obtained in Example 2 according to the present invention.

The procedure of Example 1 was repeated with the exception that xylene was used as a solvent. The compound was analyzed by IR and GPC, and the results were shown in FIG. 3 and FIG. 4.

Comparative Example 1

Figure 5:
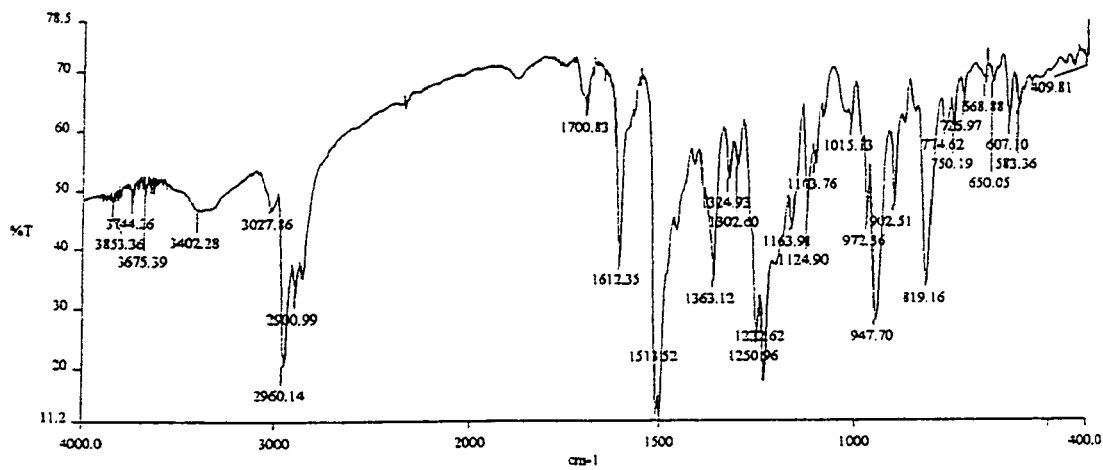
FIG. 5 is an IR spectrum of the azaoxa heterocyclic compound obtained in Example 3 according to the present invention.
Figure 6:
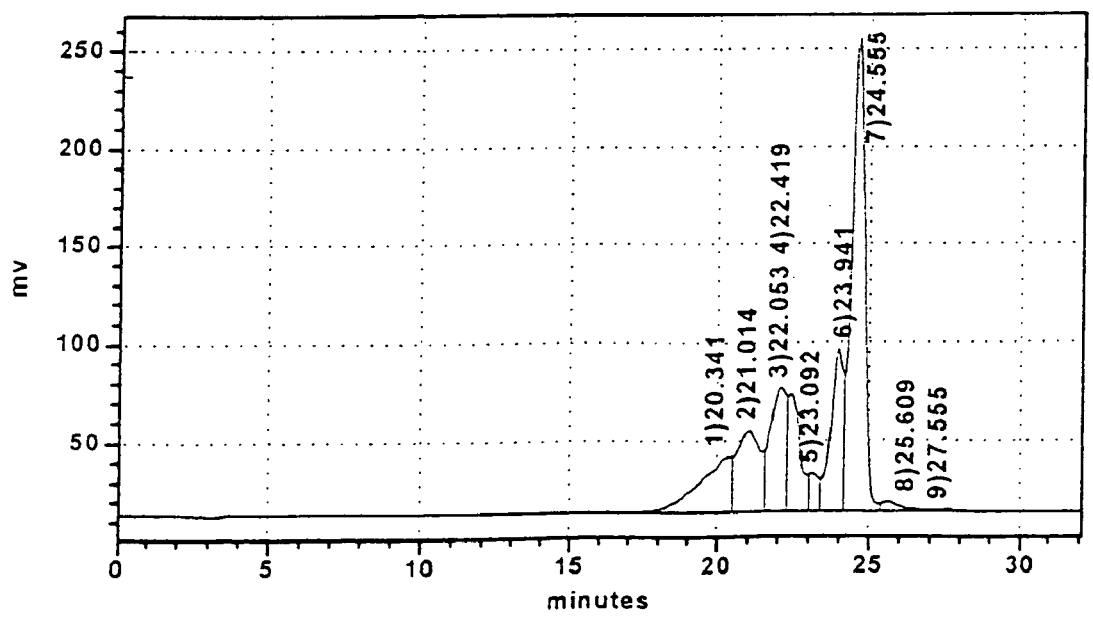
FIG. 6 is a GPC spectrum of the azaoxa heterocyclic compound obtained in Example 3 according to the present invention.

The procedure of Example 1 was repeated with the exception that methyl ethyl ketone was used as a solvent. The compound was analyzed by IR and GPC, and the results were shown in FIG. 5 and FIG. 6.

Example 3

Figure 7:
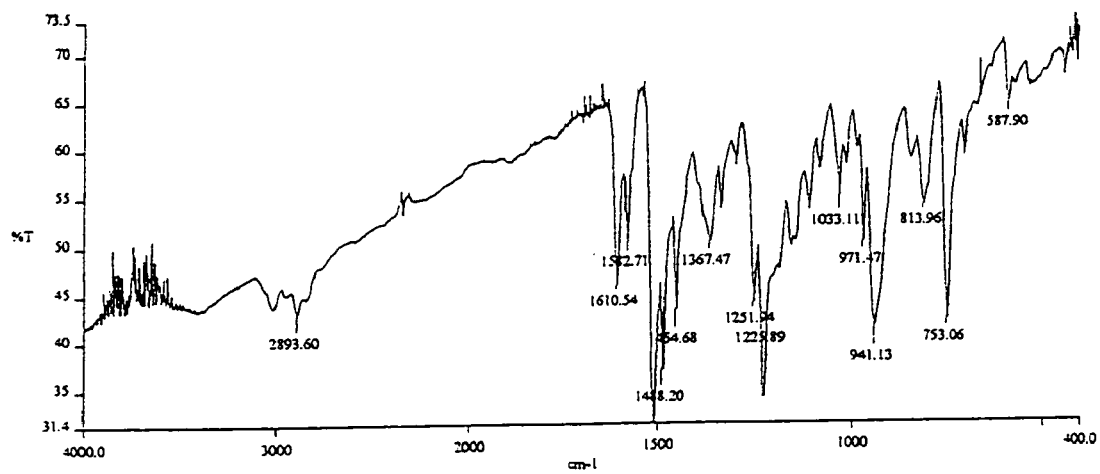
FIG. 7 is an IR spectrum of the azaoxa heterocyclic compound obtained in Example 4 according to the present invention.
Figure 8:
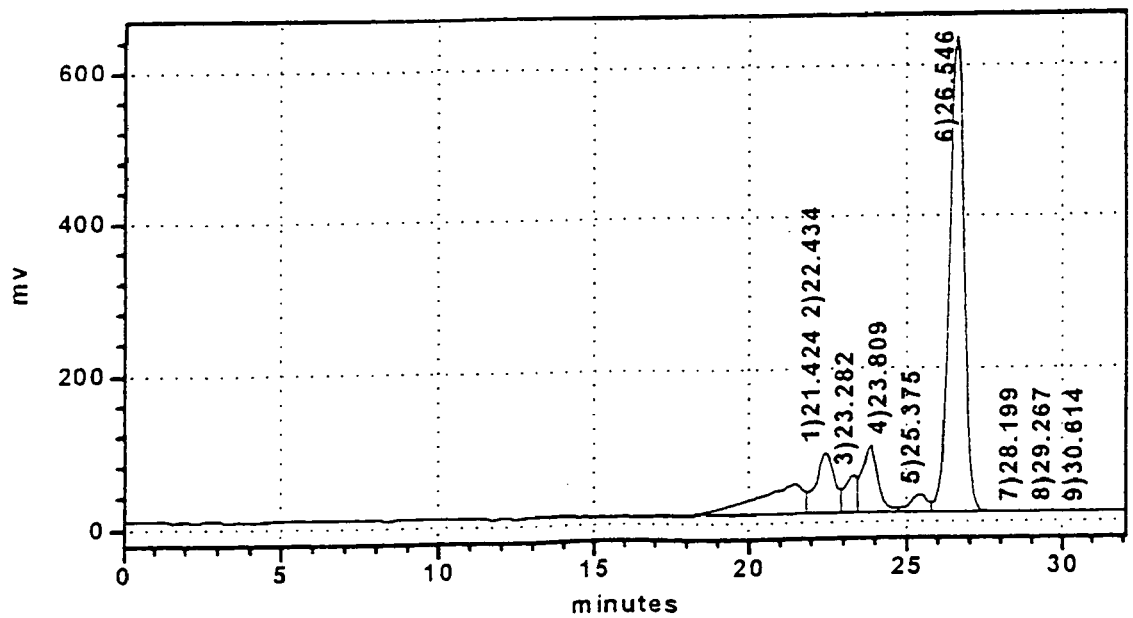
FIG. 8 is a GPC spectrum of the azaoxa heterocyclic compound obtained in Example 4 according to the present invention.

240 g of dianilinomethane, 228 g of phenol, 156.8 g of 92% of paraformaldehyde and 300 g of toluene were successively charged into a 1L of four-neck reaction vessel equipped with a stirrer, thermometer, pressure reducing system, and condensing-heating mantle. After heated up to 50° C., the electric source for heating was shut. The reaction is conducted for 2.5 hours while maintaining the temperature in the range of 85 and 90° C. Subsequently, in order to recover toluene, the internal pressure was reduced and the temperature was raised. After reaching the temperature of 130° C. and the vacuum pressure of more than 650 mm Hg and after recovering all of toluene, the solid azaoxa heterocyclic compound having the benzoxazine cyclic structure of the present invention was discharged. Alternatively, the solvent can be directly charged into the reaction vessel, and the azaoxa heterocyclic compound was present in a solvent form. The compound was analyzed by IR and GPC, and the results were shown in FIG. 7 and FIG. 8.

Example 4

Figure 9:
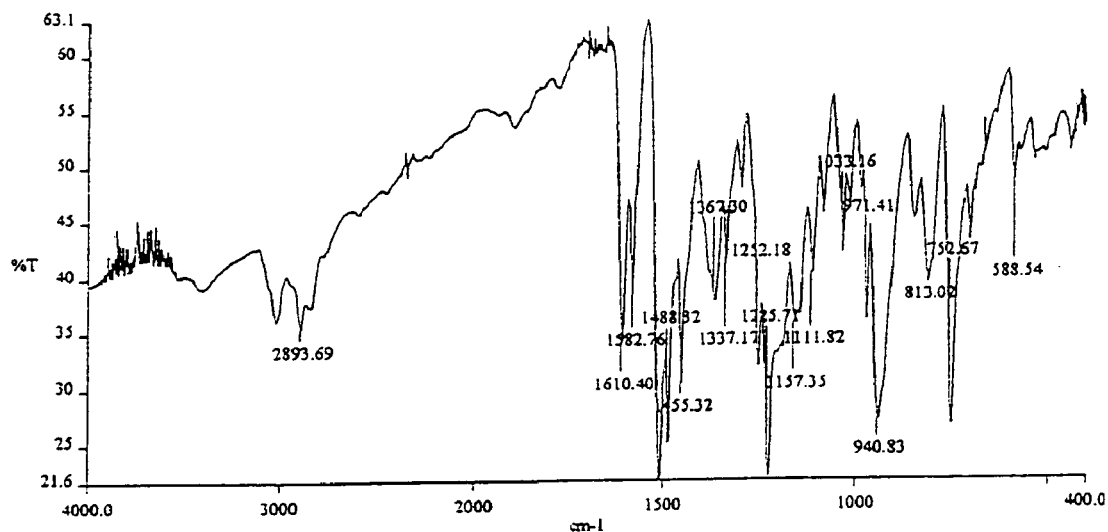
FIG. 9 is an IR spectrum of the azaoxa heterocyclic compound obtained in Example 5 according to the present invention.
Figure 10:
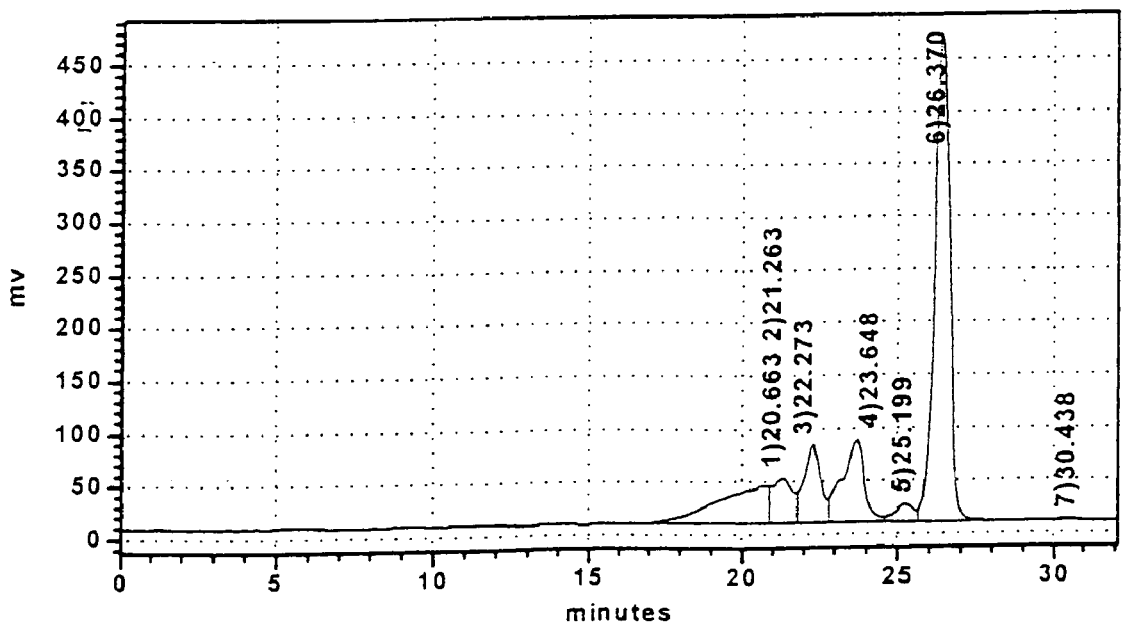
FIG. 10 is a GPC spectrum of the azaoxa heterocyclic compound obtained in Example 5 according to the present invention.

The procedure of Example 3 was repeated with the exception that xylene was used as a solvent. The compound was analyzed by IR and GPC, and the results were shown in FIG. 9 and FIG. 10.

Comparative Example 2

Figure 11:
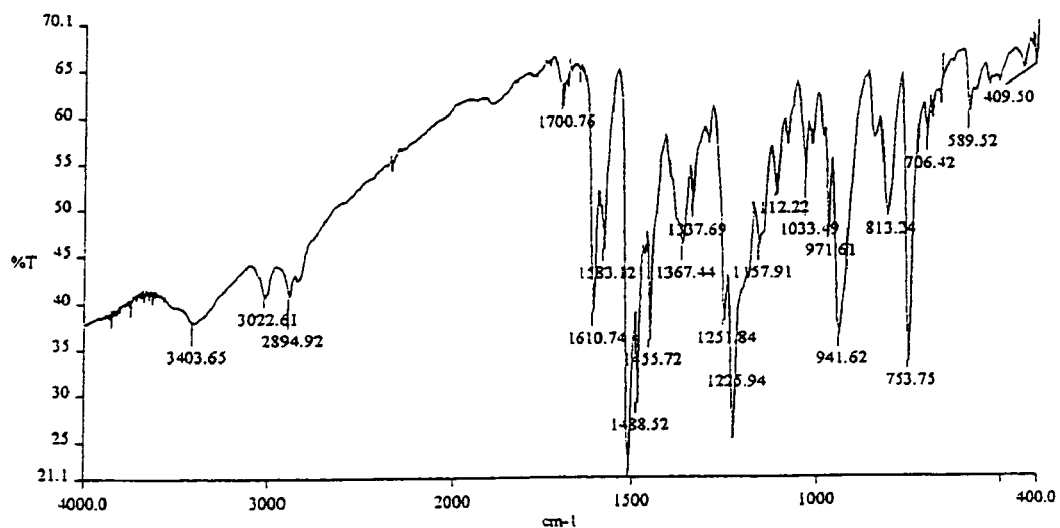
FIG. 11 is an IR spectrum of the azaoxa heterocyclic compound obtained in Comparative Example 1 according to the present invention.
Figure 12:
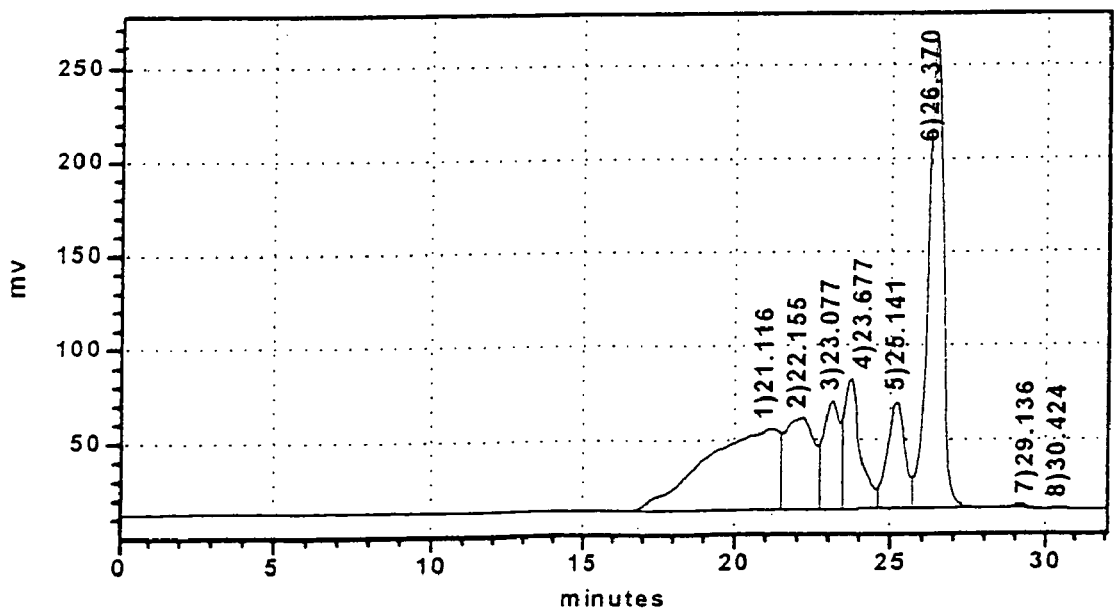
FIG. 12 is a GPC spectrum of the azaoxa heterocyclic compound obtained in Comparative Example 1 according to the present invention.

The procedure of Example 3 was repeated with the exception that methyl ethyl ketone was used as a solvent. The compound was analyzed by IR and GPC, and the results were shown in FIG. 11 and FIG. 12.

The system using hydrocarbon compound as a solvent existed relatively low gelation or agglomeration and was relatively stable comparing with the system using methyl ethyl ketone as a solvent.

Preparation of Samples

According to the ratios shown in Table 1, epoxy resins, a hardener, a hardening promoter and a solvent were formulated an epoxy resin varnish in a vessel equipped with a stirrer and a condenser:

BEB530A80 represents a bisphenol A type epoxy resin with low bromine content manufactured by Chang Chun Plastics Co., Ltd., and the epoxy equivalent weight thereof is in the range of 420 to 450 g/eq. The hydrolytic chlorine content is below 500 ppm, the bromine content is in the range of 18 to 20 weight % , and the solid content is the range of 79 to 81 weight % . The solvent is acetone. The viscosity is in the range of 1200 to 1800 cps/25° C.

BEB580A75 represents a high heat resistant epoxy resin with low bromine content manufactured by Chang Chun Plastics Co., Ltd., and the epoxy equivalent weight thereof is in the range of 300 to 340 g/eq. The hydrolytic chlorine content is below 500 ppm, the bromine content is in the range of 23 to 26 weight %, and the solid content is the range of 74 to 76 weight %. The solvent is acetone.

TNE190A70 represents a multi-functional epoxy resin manufactured by Chang Chun Plastics Co., Ltd., and the epoxy equivalent weight thereof is in the range of 200 to 220 g/eq. The hydrolytic chlorine content is below 1000 ppm, and the solid content is the range of 69 to 71 weight %. The solvent is acetone. The viscosity is in the range of 50 to 200 cps/25° C.

PF3800M60 represents an azaoxa heterocyclic compound prepared from phenol, dianilinomethane and paraformaldehyde, which was manufactured by Chang Chun Plastics Co., Ltd.

PF3900M60 represents an azaoxa heterocyclic compound prepared from p-t-butylphenol, dianilinomethane and paraformaldehyde, which was manufactured by Chang Chun Plastics Co., Ltd.

TABLE 1

|  | Sample 1 | Sample 2 | Sample 3 | Sample 4 |
|---|---|---|---|---|
| BEB530A80(g) | — | 200 | — | 200 |
| BEB580A75(g) | 200 | — | 200 | — |
| TNE190A70(g) | 3.0 | 4.6 | 3.0 | 4.6 |
| PF3800M60(g) | — | — | 191 | 155 |
| PF3900M60(g) | 237 | 91 | — | — |
| 10% 2MI | 2.33 | 3.3 | 2.25 | 3 |
| Propyleneglycol momomethyl ether | 0 | 21 | 8 | 23 |

A glass-fiber fabric was impregnated in the epoxy resin varnish prepared above, then dried at 160° C. for 8 to 10 minutes so that prepregs were formed. Eight pieces of the above prepregs were piled up, and a sheet of 35 µm copper foil was placed on the top and bottom sides of the eight prepregs, then laminated at 185° C. under a pressure of 25 kg/cm² to form a laminated entities of the prepregs and the glass fiber fabric. The glass transition temperature was measured by DSC (Differential Scan Calorimeter, TA 2910) (the temperature is in the range of 50 to 250° C., a rate of temperature rise is 20° C./min). The inflammability was measured by a flame test according to the method of UL746. Th resulting prepreg specimen is cut into five pieces of 12.5 mm×1.3 mm. A flame is applied to each piece twice. The sum of the combustion periods for ten tests must not exceed 50 seconds, and the combustion period for each test must not exceed 10 seconds to pass the burning test.

TABLE 2

The inflammability and the glass-transition temperatures of films after baking at 150° C. for 120 minutes.

|  | Sample 1 | Sample 2 | Sample 3 | Sample 4 |
|---|---|---|---|---|
| The sum of the combustion periods (sec.) | 15 | 18 | 17 | 22 |
| Tg (° C.) | 189.5° C. | 145.3° C. | 191.6° C. | 144.6° C. |

Results of physical property tests on each laminate are shown in Table 3.

TABLE 3

| Test Item | Sample 1 | Sample 2 | Sample 3 | Sample 4 |
|---|---|---|---|---|
| Tg (° C.) | 192.5° C. | 145.3° C. | 191.6° C. | 144.6° C. |
| Burning Test | pass | pass | pass | pass |
| Solder Resistance (288° C.) | >300 sec. | >300 sec. | >300 sec. | >300 sec. |
| Peeling Strength (kgf/cm) | 1.7 | 1.9 | 1.7 | 1.9 |
| Surface Resistance | $3.9 * 10^{14}$ | $2.6 * 10^{14}$ | $5.5 * 10^{14}$ | $1.78 * 10^{14}$ |
| Volume Resistance | $6.2 * 10^{15}$ | $7.2 * 10^{15}$ | $3.1 * 10^{15}$ | $6.9 * 10^{15}$ |
| Dielectric Constant | 4.4 | 4.5 | 4.5 | 4.6 |
| Dissipation Coefficient | 0.009–0.011 | 0.013–0.015 | 0.009–0.012 | 0.013–0.016 |
| water absorbency | 0.262% | 0.214% | 0.373% | 0.326% |

As shown in Table 3, in the same resin system the water absorbency of the laminate manufactured by using the azaoxa heterocyclic compound (PF3900) prepared from alkylphenol as a hardener was apparently decreased 30% comparing with that of the laminate manufactured by using the azaoxa heterocyclic compound (PF3800) prepared from phenol as a hardener.

Although the present invention was described above with reference to the examples, the present invention is not limited thereto, and various modification and additions may be made without departing from the spirit of the invention which is defined by the following claims.

What is claimed is:

1. A method for preparing the azaoxa heterocyclic compound, comprising undergoing the polymerization reaction of phenolic compound, amine compound and aldehyde compound using a hydrocarbon solvent to form the compound having the benzoxazine cyclic structure, wherein at least one of hydrogen atoms on ortho-positions to the hydroxy group in the phenolic compound is unsubstituted and the amine compound is a primary amine compound.

2. The method according to claim 1, wherein the phenolic compound is represented by the following formula (II):

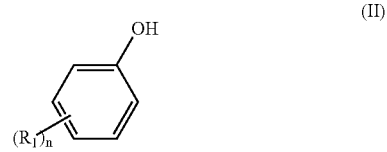

(II)

wherein $R_1$ is selected from the group consisting of an alkyl group, an alkenyl group, an alkoxyl group, a hydroxy group, halogen and an amino group; and n is an integer from 1 to 4.

3. The method according to claim 2, wherein the phenolic compound is an alkylphenol.

4. The method according to claim 3, wherein the alkylphenol is p-t-butylphenol.

5. The method according to claim 3, wherein the amine compound is an aromatic diamine compound.

6. The method according to claim 5, wherein the aromatic diamine compound is represented by the following formula (III):

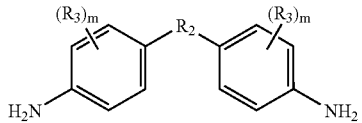

wherein $R_2$ is selected from the group consisting of a bond, an alkylene group, O, S and $SO_2$; $R_3$ is H or $C_1$–$C_6$ alkyl group; and m is an integer from 0 to 4.

7. The method according to claim 1, wherein the aldehyde is formaldehyde or paraformaldehyde.

8. The method according to claim 1, wherein the hydrocarbon solvent is one selected from aliphatic hydrocarbon solvents, alicyclic hydrocarbon solvents, aromatic hydrocarbon solvents and liquid state olefin compounds.

9. The method according to claim 8, wherein the hydrocarbon solvent is an aromatic hydrocarbon solvent.

10. The method according to claim 9, wherein the aromatic hydrocarbon solvent is toluene.

11. The method according to claim 9, wherein the aromatic hydrocarbon solvent is xylene.

* * * * *